(12) United States Patent
Bara et al.

(10) Patent No.: US 7,651,994 B2
(45) Date of Patent: Jan. 26, 2010

(54) FRAGRANCE COMPOSITIONS COMPRISING DECAMETHYLTETRASILOXANE

(75) Inventors: Isabelle Bara, La Varenne St Hilaire (FR); Daniel Buet, L'Hay les Roses (FR)

(73) Assignee: L'Oreal, Paris (FR)

( * ) Notice: Subject to any disclaimer, the term of this patent is extended or adjusted under 35 U.S.C. 154(b) by 449 days.

(21) Appl. No.: 11/111,703

(22) Filed: Apr. 22, 2005

(65) Prior Publication Data

US 2005/0245430 A1    Nov. 3, 2005

Related U.S. Application Data

(60) Provisional application No. 60/577,597, filed on Jun. 8, 2004.

(30) Foreign Application Priority Data

Apr. 29, 2004    (FR)  ................... 04 50824

(51) Int. Cl.
*A61Q 13/00*    (2006.01)
*A61K 8/25*    (2006.01)
*A61K 8/34*    (2006.01)
*C08L 83/04*    (2006.01)

(52) U.S. Cl. ........................... 512/1; 524/588

(58) Field of Classification Search ................ None
See application file for complete search history.

(56) References Cited

U.S. PATENT DOCUMENTS

| 5,665,339 | A | 9/1997 | Simmons |
| 6,403,109 | B1 | 6/2002 | Stora |
| 2003/0190255 | A1* | 10/2003 | Boden et al. .................. 422/5 |

FOREIGN PATENT DOCUMENTS

EP    0 566 240 A1    10/1993

OTHER PUBLICATIONS

French Search Report corresponding to FR 04/50824 issued on Jan. 24, 2005, 2 pages.

* cited by examiner

*Primary Examiner*—Michael J Feely
(74) *Attorney, Agent, or Firm*—Buchanan, Ingersoll & Rooney P.C.

(57) ABSTRACT

Novel fragrance compositions containing: (a) a mixture of odoriferous materials in an amount of 11% to 25% of the total weight of the composition, (b) ethanol in an amount of 65 to 80% of the total weight of the composition, (c) decamethyltetrasiloxane in an amount of 3% to 22% of the total weight of the composition, (d) water in an amount not exceeding 7% of the total weight of the composition, and (e) a surfactant in an amount greater than 0% to less than 0.5% of the total weight of the composition. The fragrance compositions retain a visual appearance and olfactory characteristics, which are stable over time, and have a flash point generally of greater than or equal to 15° C.

7 Claims, No Drawings

FRAGRANCE COMPOSITIONS COMPRISING DECAMETHYLTETRASILOXANE

CROSS-REFERENCE TO PRIORITY/PROVISIONAL APPLICATIONS

This application claims priority under 35 U.S.C. § 119 of FR 04/50824, filed Apr. 29, 2004, and of provisional application Ser. No. 60/577,597, filed Jun. 8, 2004, each hereby expressly incorporated by reference and each assigned to the assignee hereof.

BACKGROUND OF THE INVENTION

1. Technical Field of the Invention

The present invention relates to novel fragrance/perfume compositions comprising:

(a) from 11% to 60% by weight of a mixture of odoriferous materials, (b) from 51% to 80% by weight of ethanol, and (c) from 3% to 30% by weight of decamethyltetrasiloxane, with respect to the total weight of the composition.

2. Description of Background and/or Related and/or Prior Art

Fragrance compositions usually comprise a mixture of odoriferous materials which have a vapor pressure of less than atmosphere pressure at 25° C. and which are generally liquid at 25° C., but which are sometimes also solid, in a physiologically acceptable medium based on ethanol and optionally on water.

Ethanol is a good dissolving agent for perfuming ingredients and exhibits, in addition, the advantage of being inexpensive and of making possible the formulation of transparent compositions. On the other hand, it has the disadvantage of reacting chemically with nitrogen oxides in the atmosphere to form ozone and therefore constitutes a source of atmospheric pollution which it is desirable to avoid.

It is therefore usual to replace a portion of the ethanol with water. However, water and ethanol are not chemically inert and react with the compounds of the fragrances, producing, over time, olfactory changes of a detrimental nature and/or modifications in the appearance of the liquids (yellowing, browning). The chemical reactions responsible for this deterioration are mainly:

- the formation of acetals, by condensation of ethanol with chemical compounds comprising an aldehyde functional group;
- the saponification or hydrolysis of compounds comprising an ester functional group;
- the oxidation of monoterpenes or sesquiterpenes present particularly in plant extracts; and
- the oxidation of ethanol to acetaldehyde and then to acetaldehyde diethyl acetal (DEA), accompanied by the formation of acetic acid and then of ethyl acetate.

In addition, water is not a good solvent for fragrances and reduces the solvating power of ethanol. Problems of cloudiness or of dissolution sometimes appear from the beginning of the formulation of the fragrances and necessitate a significant reduction in the level of fragrance. This results in more dilute fragrances, whereas the current trend is to produce fragrances which are instead strong and highly concentrated (more than 10% of perfuming materials).

The advantage in substituting, for the water present in fragrances, another starting material which is inert, which is volatile, which has good miscibility with ethanol and which makes it possible to dissolve large amounts of perfuming ingredients is thus apparent.

SUMMARY OF THE INVENTION

It is now surprisingly and unexpectedly been determined that a specific polydimethylsiloxane, decamethyltetrasiloxane, satisfies this objective in the presence of a high concentration of ethanol. The fragrance compositions thus obtained make it possible to produce an economically acceptable compromise by retaining a large amount of ethanol, which is cheap, without loss of stability or a detrimental change in the olfactory characteristics of the fragrance over time.

U.S. Pat. No. 5,665,339 relates to fragrance compositions comprising at most 10% of fragrance, from 10% to 90% of ethanol, from 10% to 90% of a polydimethylsiloxane, such as decamethyltetrasiloxane, and less than 1% of water. However, the polydimethylsiloxane is said to be used to improve the cosmetic quality and to reduce the irritation brought about by alcohol-comprising lotions. There is no suggestion that permits the formulation of fragrance compositions including more than 10% of perfuming ingredients.

Furthermore, WO 99/01106 discloses compositions intended for scenting textiles without staining them which include from 0.1% to 90% of fragrance, from 10% to 99.9% of volatile silicone, such as decamethyltetrasiloxane, optionally ethanol (at most 10%) and less than 1% of water. These compositions do not include a sufficient amount of ethanol to make possible good dissolution of the fragrance at an economically reasonable cost and may in addition be responsible for an undesirable penetration of the fragrance into the skin.

U.S. Pat. No. 5,160,494 discloses anhydrous fragrance compositions including from 5% to 30% of fragrance, from 1% to 95% of alkylmethyldisiloxane, intended to replace ethanol, which can, all the same, represent from 0% to 90% of the weight of the composition, and optionally from 0% to 40% of silicones, such as decamethyltetrasiloxane. This patent does not suggest that the decamethyltetrasiloxane can make it possible to lower the level of alcohol while maintaining it at an economically acceptable level and without necessarily requiring recourse to an expensive alkylmethyldisiloxane.

U.S. Patent Published Applications 2003/0190267 and 2003/0190255 disclose air freshener compositions which do not generate deposits and which comprise from 0.01% to 50%, preferably from 15% to 25%, of ethanol, from 20% to 30% (respectively from 14% to 40%) of a silicone, such as decamethyltetrasiloxane, and at most 5% of water. The examples given in these patent applications comprise more than 10% of fragrances. The suggestion is not made, in these patent applications, to formulate fragrance compositions including more than 50% of ethanol, which would on the contrary risk presenting problems of safety in view of their flammability, as regards air fresheners. In addition, a composition having a flash point in the region of 20° C. is not disclosed, insofar as the flash point is instead in the region of 60° C.

The present invention thus features fragrance compositions comprising: (a) from 11% to 60% by weight of a mixture of odoriferous materials, (b) from 51% to 80% by weight of ethanol and (c) from 3% to 30% by weight of decamethyltetrasiloxane, with respect to the total weight of the composition.

DETAILED DESCRIPTION OF BEST MODE AND SPECIFIC/PREFERRED EMBODIMENTS OF THE INVENTION

The odoriferous materials present in the fragrance compositions according to the invention are compounds conventionally used by perfumers and they are described in particular in S. Arctander, *Perfume and Flavor Chemicals* (Montclair, N.J., 1969), in S. Arctander, *Perfume and Flavor Materials of Natural Origin* (Elizabeth, N.J., 1960), and in *Flavor and Fragrance Materials*—1991, Allured Publishing Co. Wheaton, Ill., USA.

They can be natural products (essential oils, absolutes, resinoids, resins or concretes) and/or synthetic products (hydrocarbons, alcohols, aldehydes, ketones, ethers, acids, esters, acetals, ketals or nitriles, which may be saturated or unsaturated and aliphatic or cyclic).

Examples of essential oils comprise essential oils of lemon, orange, anise, bergamot, rose, geranium, ginger, neroli, basil, rosemary, cardamom, camphor, cedar, camomile, sandalwood or sage, and their mixtures, without this list being limiting.

Examples of other odoriferous compounds are in particular: geraniol, geranyl acetate, farnesol, borneol, bornyl acetate, linalol, linalyl acetate, linalyl propionate, linalyl butyrate, tetrahydrolinalol, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)-propanal, 3-(p-tert-butylphenyl) propanal, 2,4-dimethylcyclohex-3-enecarboxaldehyde, tricyclodecenyl acetate, tricyclodecenyl propionate, 4-(4-hydroxy-4-methylpentyl)-3-cyclohexenecarboxaldehyde,4-(4-methyl-3-pentenyl)-3-cyclohexenecarboxaldehyde,4-acetoxy-3-pentyltetrahydropyran, 2-(n-heptyl)cyclopentanone, 3-methyl-2-pentyl-2-cyclopentanone, menthone, carvone, tagetone, geranylacetone, n-decanal, n-dodecanal, 9-decen-1-ol, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, anisonitrile, anisaldehyde, heliotropin, coumarin, eugenol, vanillin, diphenyl ether, citral, citronellal, hydroxycitronellal, damascone, ionones, methylionones, isomethylionones, solanone, irones, cis-3-hexenol and its esters, indane musk compounds, tetralin musk compounds, isochroman musk compounds, macrocyclic ketones, macrolactone musk compounds, ethylene brassylate and their mixtures.

The compositions according to the present invention include from 11% to 60% by weight and preferably from 11% to 25% by weight of odoriferous materials.

Same also contain ethanol and decamethyltetrasiloxane, generally in an amount sufficient to dissolve these odoriferous materials and to confer, on the composition, a flash point of greater than or equal to 15° C. and preferably of less than or equal to 60° C. Thus, the amount of ethanol represents from 51% to 80% and preferably from 51% to 65% of the weight of the composition, the amount of decamethyltetrasiloxane representing from 3% to 30% and preferably from 10% to 30% of the weight of the composition.

Decamethyltetrasiloxane is available in particular from Dow Corning under the trade name DC 200 Fluid 1.5 cSt.

The fragrance compositions according to the invention also generally comprise solvents, adjuvants or additives commonly used in the field of perfumery which do not harm the desired olfactory effect.

Thus, the compositions according to the invention can comprise a small amount of water, generally not exceeding 7% of the total weight of the composition, which can in particular be contributed by the ethanol, the latter generally being sold in the form of a mixture of denatured alcohol and of water.

In addition, according to a preferred embodiment, the compositions according to the invention do not comprise alkyldimethylsiloxane in which the alkyl group contains from 2 to 13 carbon atoms.

In addition, the stability of the compositions according to the invention is such that they do not require the presence of a surface-active agent. Thus, according to a preferred embodiment of the invention, this composition includes less than 1% by weight, indeed even less than 0.5% by weight, of surfactant, indeed even no surfactant at all.

The subject fragrance compositions can constitute an eau de cologne, an eau de toilette, a fragrance or an aftershave lotion.

Depending on its flash point, the subject compositions can be packaged in an atomizer or optionally in an aerosol device. In the latter case, the composition according to the invention additionally comprises a propellant gas, such as dimethyl ether, propane, n-butane, isobutane, pentane, trichlorofluoromethane, dichlorodifluoromethane, chlorodifluoromethane, 1,1,1,2-tetrafluoroethane, chloropentafluoroethane, 1-chloro-1,1-difluoroethane, 1,1-difluoroethane and their mixtures. Use is preferably made of dimethyl ether, isobutane and 1,1,1,2-tetrafluoroethane and preferentially of isobutane.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Comparative Study of the Properties of Different Silicone-Comprising Fragrance Compositions Four fragrance compositions were tested in order to evaluate their flash points and their cosmetic properties.

In order to measure the flash point, each test composition is heated for 60 seconds in a closed cup of standardized dimensions at a temperature approximately 3° C. lower than the assumed flash point. A flame of standardized size is then introduced into the vapors of the cup via a sliding opening. The test is repeated in steps of 1° C. The lowest temperature at which ignition occurs is recorded as being the flash point. The test is carried out on a Setaflash device according to Standard ISO 3679.

The four test compositions each included: 12% of fragrance, 22% of a polydimethylsiloxane (PDMS), the nature of which varied according to the compositions, and 66% of ethanol comprising 93.5% by weight of denatured alcohol.

The results obtained for the four test compositions are reported in the Table below:

TABLE

| Composition | PDMS | Flash point | Cosmetic properties |
|---|---|---|---|
| A | L2 (hexamethyldisiloxane) | −5° C. | satisfactory |
| B | L3 (octamethyltrisiloxane) | 13° C. | satisfactory |
| C | L4 (decamethyltetrasiloxane) | 17° C. | satisfactory |
| D | L5 (dodecamethylpentasiloxane) | 17° C. | oily effect |

As seen from this table, only the silicone of L4 type makes it possible to obtain, in combination with the ethanol, a composition having a flash point which allows it to be manufactured industrially while having good sensory properties.

Example 2

Comparative Study of the Stability of Fragrance Compositions

The stability over time of three fragrance compositions was tested:
- the above composition C in which the fragrance corresponded to the perfume extract "Volupté" from Gloria Vanderbilt
- a composition C' comprising 12% of the same fragrance, 66% of ethanol comprising 93.5% by weight of denatured alcohol, and 22% of water instead of the decamethyltetrasiloxane,
- a composition C" corresponding to the composition C' to which 0.05% of BHT has been added as antioxidant.

Visual and Olfactory Aspects:

After storage at ambient temperature and at 45° C. for 2 months, the composition C' exhibited a pronounced olfactory deterioration and a significant browning. The composition C" exhibited a moderate olfactory deterioration and a still significant browning. In contrast, the composition C retained a clear, colorless and homogeneous appearance and an excellent olfactory stability, even after storage at ambient temperature and at 45° C. for six months.

Chemical Stability:

The compositions C, C' and C" were analyzed after three months at 45° C. The following were observed for the composition C:
- reduced formation of diethyl acetals, which is reflected by five times less hydroxycitronellal DEA formed, with respect to the composition C',
- virtual absence of linalol, geraniol and nerol, decomposition products of linalyl acetate, whereas the compositions C' and C" underwent approximately 50% decomposition of the linalyl acetate,
- virtual absence of benzyl alcohol and of benzaldehyde, decomposition products of benzyl acetate, whereas the compositions C' and C" underwent approximately 1% decomposition of benzyl acetate, which is very strongly odorous,
- virtual absence of limonene, myrcene and ocimeme oxides, oxidation products of terpenes, whereas the composition C' underwent approximately 40% decomposition of the limonene, and
- very limited oxidation of the ethanol, which is reflected by the presence of 60 ppm of acetaldehyde DEA and the absence of ethyl acetate, whereas, for the composition C', 900 ppm of acetaldehyde DEA and 110 ppm of ethyl acetate were measured.

These results show the good chemical stability of the compositions according to the invention, which make it possible to avoid the formation of decomposition products of the fragrances, some of which are potential allergens.

Example 3

Comparative Study of the Solubilization of the Fragrance

The visual appearance of two fragrance compositions C1 and C'1, corresponding respectively to the composition C of Example 2 in which the fragrance was the perfume extract "Eau de Lancôme" and to the composition C' of Example 2 including the same perfume extract, was compared.

The composition C'1 exhibited a cloudy appearance from its preparation. In contrast, the composition C1 existed in the form of a perfectly clear homogeneous mixture stable at ambient temperature and at 45° C. for two months.

This test illustrates the ability of the ethanol/silicone mixtures according to the invention to dissolve high concentrations of fragrances, in comparison with conventional aqueous/alcoholic solutions.

Example 4

Fragrance Compositions

The compositions below are prepared in conventional manner:

| Composition A: | |
|---|---|
| Perfume extract "Noa" | 15% |
| Decamethyltetrasiloxane | 10% |
| Ethanol | 75% |
| Composition B: | |
| Perfume extract "Emporia White She" | 20% |
| Decamethyltetrasiloxane | 15% |
| Ethanol | 65% |
| Composition C: | |
| Perfume extract "Attraction" | 30% |
| Decamethyltetrasiloxane | 5% |
| Ethanol | 65% |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A fragrance composition consisting essentially of:
   (a) from 11% to 25% by weight of admixture of odoriferous materials,
   (b) from 65% to 80% by weight of ethanol,
   (c) from 3% to 22% by weight of decamethyltetrasiloxane,
   (d) water in an amount not exceeding 7% of the total weight of the composition, and (e) greater than 0% to less than 0.5% of surfactant,
wherein the composition has a flash point of greater than or equal to 15° C., and each based on the total weight of the composition.

2. The fragrance composition as defined by claim 1, comprising from 10% to 22% by weight of decamethyltetrasiloxane.

3. The fragrance composition as defined by claim 1, devoid of any alkyldimethylsiloxane in which the alkyl group contains from 2 to 13 carbon atoms.

4. The fragrance composition as defined by claim 1, packaged in an aerosol dispenser.

5. The fragrance composition as defined by claim 1, having a flash point of less than or equal to 60° C.

6. The fragrance composition as defined by claim 1, wherein said admixture of odoriferous materials comprises an essential oil of lemon, orange, anise, bergamot, rose, geranium, ginger, neroli, basil, rosemary, cardamom, camphor, cedar, camomile, sandalwood, or sage, or other odoriferous compound selected from the group consisting of geraniol, geranyl acetate, farnesol, borneol, bornyl acetate, linalol, linalyl acetate, linalyl propionate, linalyl butyrate, tetrahydrolinalol, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)propanal, 2,4-dimethylcyclohex-3-enecarboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 2-(n-heptyl)cyclopentanone, 3-methyl-2-pentyl-2-cyclopentanone, menthone, carvone, tagetone, geranylacetone, n-decanal, n-dodecanal, 9-decen-1-ol, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, anisonitrile, anisaldehyde, heliotropin, coumarin, eugenol, vanillin, diphenyl ether, citral, citronellal, hydroxycitronellal, damascone, ionone, methylionone, isomethylionone, solanone, irone, cis-3-hexenol or ester thereof, indane musk compound, tetralin musk compound, isochroman musk compound, macrocyclic ketone, macrolactone musk compound, ethylene brassylate and any mixture thereof 7. The fragrance composition as defined by claim 1, formulated as an eau de cologne, an eau de toilette, a perfume or an aftershave lotion.

\* \* \* \* \*